(12) United States Patent
Petisce et al.

(10) Patent No.: US 11,311,667 B2
(45) Date of Patent: Apr. 26, 2022

(54) INSULIN LEAKAGE SENSOR WITH ELECTRIC CONTROL TO STOP INSULIN FLOW

(71) Applicant: Becton, Dickinson and Company, Franklin Lakes, NJ (US)

(72) Inventors: James R. Petisce, Westford, MA (US); Eric Bene, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 212 days.

(21) Appl. No.: 16/500,619

(22) PCT Filed: Apr. 19, 2018

(86) PCT No.: PCT/US2018/028361
§ 371 (c)(1),
(2) Date: Oct. 3, 2019

(87) PCT Pub. No.: WO2018/195310
PCT Pub. Date: Oct. 25, 2018

(65) Prior Publication Data
US 2020/0188585 A1   Jun. 18, 2020

Related U.S. Application Data

(60) Provisional application No. 62/488,005, filed on Apr. 20, 2017.

(51) Int. Cl.
*A61M 5/168* (2006.01)
*A61M 5/142* (2006.01)
(52) U.S. Cl.
CPC .... *A61M 5/16831* (2013.01); *A61M 5/14248* (2013.01); *A61M 5/16881* (2013.01); *A61M 2205/15* (2013.01)

(58) Field of Classification Search
CPC .......... A61M 5/16831; A61M 5/16836; A61M 5/1413; A61M 5/14244; A61M 2005/14248; A61M 2205/15
See application file for complete search history.

(56) References Cited

U.S. PATENT DOCUMENTS 6,461,329 B1 * 10/2002 Van Antwerp .... A61M 5/16836
604/111
6,932,114 B2 * 8/2005 Sparks .............. A61M 5/16827
137/814

(Continued)

FOREIGN PATENT DOCUMENTS

EP       3144023 A1     3/2017

OTHER PUBLICATIONS

International Search Report dated Jul. 13, 2018, which issued in the corresponding PCT Patent Application No. PCT/US2018/028361.

*Primary Examiner* — Laura A Bouchelle
(74) *Attorney, Agent, or Firm* — Dickinson Wright PLLC

(57) ABSTRACT

An insulin delivery device (10) includes a cannula (40) for delivering insulin to a patient at an infusion site, a pump assembly (30), and a valve (36) for controlling the flow of insulin. A removable leak detector unit (28) is coupled to the delivery device for sensing and detecting leakage of insulin at the infusion site. The leak detector unit (28) has electrodes (56) positioned for contacting the insulin leaking from the infusion site, a sensing electrical circuit (54) and a power source (58) for operating the leak detector unit. The removable leak detector unit (28) has an electrical contact (62) for mating with an electrical contact (64) of the delivery device for electrically and operatively connecting the leak detector unit (28) to the delivery device. The leak detector unit (28) sends a signal to the pump assembly (30) and/or valve (36) to stop the flow of insulin when leakage is detected at the infusion site.

20 Claims, 4 Drawing Sheets

(56) References Cited

U.S. PATENT DOCUMENTS

| | | | |
|---|---|---|---|
| 8,105,280 B2 * | 1/2012 | Iddan | A61M 5/172 604/131 |
| 9,205,190 B2 * | 12/2015 | Remde | A61M 5/14244 |
| 2003/0009131 A1 | 1/2003 | Van Antwerp et al. | |
| 2003/0088238 A1 * | 5/2003 | Poulsen | A61M 5/16827 604/890.1 |
| 2008/0200897 A1 | 8/2008 | Hoss et al. | |
| 2010/0160902 A1 | 6/2010 | Aeschilimann et al. | |
| 2012/0029333 A1 | 2/2012 | Dogwiler et al. | |
| 2014/0336579 A1 | 11/2014 | Nagar et al. | |
| 2016/0158517 A1 | 6/2016 | Nebbia | |
| 2016/0317739 A1 | 11/2016 | Wang et al. | |

* cited by examiner

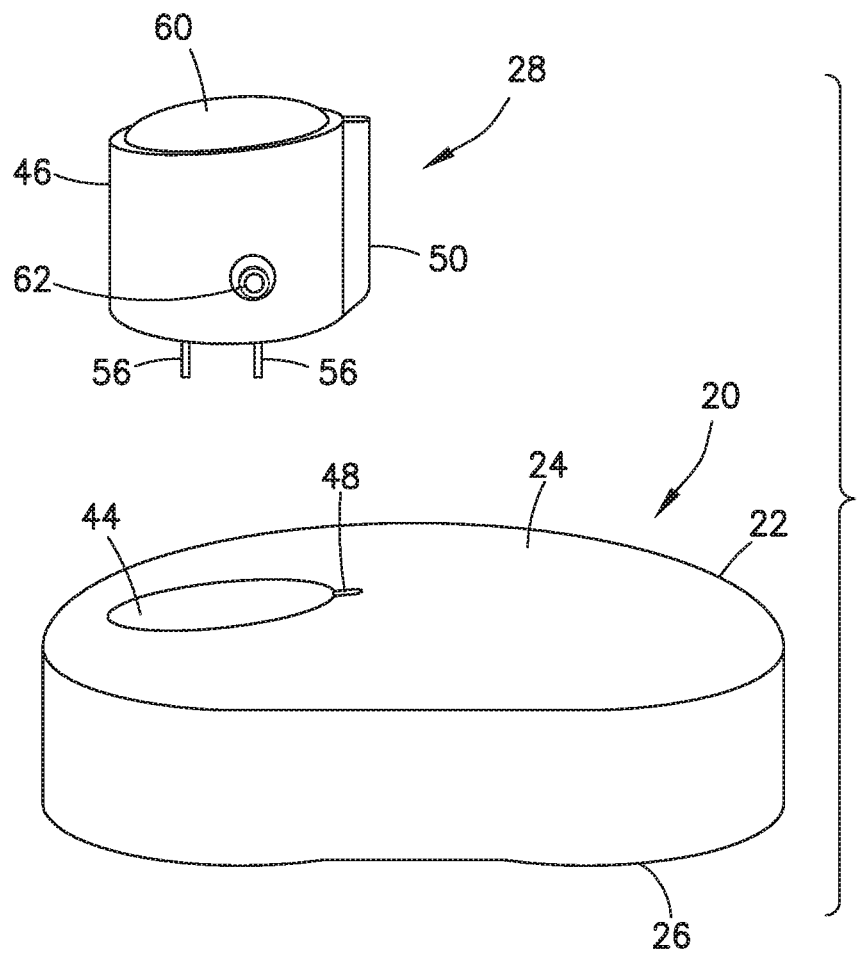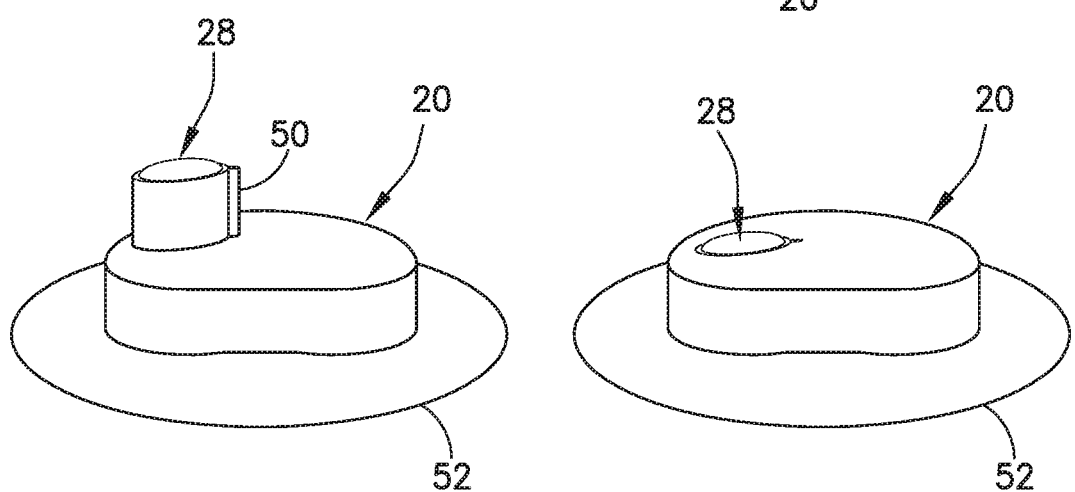
FIG.2
FIG.3
FIG.4

INSULIN LEAKAGE SENSOR WITH ELECTRIC CONTROL TO STOP INSULIN FLOW

This application claims priority to U.S. Provisional Application Ser. No. 62/488,005, filed on Apr. 20, 2017, which is hereby incorporated by reference in its entirety.

FIELD OF THE INVENTION

The present invention is directed to a delivery device with a leak detecting unit. The invention is further directed to an infusion set or patch pump assembly for delivering a medication to a patient where the infusion set or patch pump assembly has a removable leak detecting unit that controls the flow of fluid in the event of leakage at an infusion site.

BACKGROUND

There are two principal modes of daily insulin therapy. The first mode includes syringes and insulin pens. These devices are simple to use and are relatively low in cost, but they require a needle stick at each injection, typically three to four times per day. The second mode includes insulin infusion therapy, which utilizes an insulin pump. Infusion pumps, although more complex and expensive than syringes and pens, offer the advantages of continuous infusion of insulin via an infusion cannula, precision dosing, and programmable delivery schedules.

The use of an infusion pump requires the use of a disposable component, typically referred to as an infusion set, line set, extension set or pump set, which conveys the insulin from a reservoir within the pump into the skin of the user. An infusion set typically consists of a pump connector, a length of tubing, and a hub or base from which an infusion cannula (i.e., an infusion needle or a flexible catheter) extends. The hub or base has an adhesive which retains the base on the skin surface during use, and which may be applied to the skin manually or with the aid of a manual or automatic insertion device. In most cases, a detachable fluid connector is provided to allow the pump tubing to be disconnected from the hub or base of the infusion set when the user wishes to shower, bathe or swim.

There is much focus on occlusions, alarms for occlusions, and design solutions to prevent occlusions in insulin infusion pumps. However, there is no solution to a leading contributor to under-infusion, which is leakage. Leakage at the infusion site may go undetected and lead to serious adverse events. In some situations, the patient may feel wetness, or smell insulin, and thus detect a leak themselves. With some patients, and especially with lower volume infusions, self-detection of leakage may be more difficult or impossible. Undetected leakage can result in serious negative health consequences.

There are products that detect occlusions in the infusion set, but these cannot detect leakage. Accordingly, a there is a need for a system to help identify insulin leakage.

A problem with infusion sets and patch pumps occurs when the cannula separates from the skin of the patient or becomes dislodged such that leakage occurs at the infusion site. Infusion pumps generally dispense insulin in small volumes for long periods of time. When leakage occurs, it is often not noticed by the patient for an extended length of time, resulting in an improper dosage.

There are products that detect occlusions in the infusion set, but these cannot detect leakage. Accordingly, a there is a need for a system to help identify insulin leakage and stop the leakage.

Previous attempts to address insulin leakage detection have used a chemical dye positioned around the insulin infusion site. The chemical dye is capable of undergoing a color change in the presence of insulin which provides the patient with a visual indicator that insulin leakage is occurring or has occurred. The color indicators may be hidden from direct visualization by the patient due to use of infusion sites covered by clothing, out of direct view on the back, buttocks, or thigh, or obstruction by abdominal fat. When the patient sees the color change of the color changing insulin leakage detector, the patient then needs to decide what actual remedial action to take. Once the color changing insulin leakage detector has detected an insulin leakage, its useful life is over and it must be disposed. The color changing insulin leakage detector cannot be reused with a new insulin infusion sets.

Accordingly, there is a continuing need in the industry for improved delivery devices, such as infusion sets and patch pumps that provide adequate leak detection to the patient.

SUMMARY

The invention is directed to a fluid delivery device or system to provide fluid, drug, insulin or medication to a patient. The delivery device includes a leak detector that is able to detect leakage at the delivery or infusion site and control the flow of the fluid when leakage is detected.

Accordingly, one feature is to provide a fluid delivery device, an insulin delivery device, an infusion set, patch pump or other delivery device having a leak detection unit providing an indication to the patient of leakage at the infusion site.

Another feature of the invention is to provide an insulin delivery device such as an infusion set, patch pump or other insulin delivery device that provides the patient with a visible indicator that leakage has occurred at an infusion site and automatically controls or stops the flow of the insulin to the delivery device.

The delivery device in one embodiment is an infusion set or patch pump that includes a cannula or catheter for penetrating the skin of a patient for delivering a drug or other pharmaceutical agent. The infusion set or patch pump is particularly suitable for insulin delivery at a controlled rate. The infusion set or patch pump has a removable leak detector unit that detects leakage of the injected fluid at the infusion site and is connected to a pump mechanism or valve associated with the pump mechanism to stop the pump and/or close the valve to prevent further leakage. A signal or indicator is presented to the patient to notify the patient of the leakage and the cessation of the fluid flow. The patient is then able to take corrective measures to adjust or reposition the infusion set or patch pump and to continue the desired delivery.

The features are provided by a leak detector unit for use with a delivery device. The leak detector includes an electrochemical sensor having electrodes located at or near the infusion site for detecting the presence of leakage from the infusion site. A valve situated between a reservoir and the delivery device is operatively connected to the leak detector where the leak detector actuates the valve and controls and/or closes the valve to stop the flow of the substance when a leakage is detected.

The leak detector unit operatively connects to a control circuit for the valve or the pump assembly to actuate the valve or the pump assembly in controlled manner. The leak detector unit can adjust or modify the flow of the fluid, such as insulin, to reduce the flow thereby reducing or minimizing leakage while maintaining at least some flow of the insulin to the cannula. In one embodiment, the leak detector unit stops the flow completely upon detection of leakage and provides a visual or audible signal to the patient so that the patient can take corrective steps to maintain a proper infusion of insulin.

The features of the device provide a fluid delivery assembly for introducing a fluid to a patient. The delivery assembly comprises a delivery device adapted for delivering a fluid to the patient. The delivery device has a base with a bottom face for attaching to the skin of the patient, and a cannula extending from the bottom face for penetrating the skin of the patient at an infusion site. A pump assembly is connected to a fluid reservoir and the cannula for delivering the fluid through the cannula to the patient. A leak detector is coupled to the delivery device and oriented for detecting leakage of the fluid at the infusion site. The leak detector unit is operatively connected to the pump assembly to stop the pump assembly when leakage is detected at the infusion site to stop the flow of the fluid.

In one embodiment an infusion set includes a housing having a base and a cannula for introducing insulin to a patient at an infusion site. A pump assembly in the housing supplies the substance to the cannula. A leak detector detects leakage of the insulin at the infusion site. The leak detector is operatively connected to the pump mechanism to stop the flow of insulin when leakage is detected at the infusion site.

These and other features of the invention will become apparent from the following drawings and the detailed description of the invention.

BRIEF DESCRIPTION OF THE DRAWINGS

The following is a brief description of the drawings in which:

FIG. 2 is an exploded view of the delivery device having a pump mechanism and the leak detector unit;

FIG. 3 is a perspective view of one embodiment of the invention showing the leak detecting unit being inserted into the delivery device;

FIG. 4 is a perspective view showing the leak detector unit completely inserted into the delivery device in the operative position;

Throughout the drawings, the reference numbers should be understood to refer the like parts, components, and structures.

DETAILED DESCRIPTION

Described herein is a convenient, inexpensive device and method to deliver a fluid to a patient and detect the leakage of the fluid from an infusion set connected to a pump assembly. It will be appreciated that the principles described herein are also applicable to detect leakage of insulin from a delivery device, such as an infusion set and/or insulin patch pump. The colorless insulin can leak from an infusion or injection site located between the patient's outer skin surface and the bottom of an insulin infusion set or an insulin patch pump which makes insulin leakage usually not visible to the patient until the insulin leakage is excessive.

The insulin stabilizers in commercial insulins are electroactive so that the stabilizers readily oxidize upon application of a voltage. This characteristic makes insulin stabilizers suitable for detection by an electrochemical sensor. Commonly used insulin stabilizers include m-cresol and phenol.

Embodiments of the present invention provide a reusable insulin leak detector unit or sensor positioned within an opening within a delivery device, an insulin infusion set or patch pump. The patient inserts the insulin leak detector unit into the opening within the delivery device, insulin infusion set or patch pump after initially deploying the cannula and the delivery device. Upon removal of the delivery device after its useful life has expired, the patient removes the insulin leak detector unit for reuse with a new delivery device. The insulin leak detector unit is positioned at the critical interface between the patient's outer skin surface and the bottom of the delivery device.

When the insulin leak detector detects an insulin leakage, a micro-valve located upstream from the insulin infusion catheter closes after receiving a signal from the leak detector unit. Consequently, additional flow of insulin from an insulin supply which has begun leaking is prevented.

Figure 1:
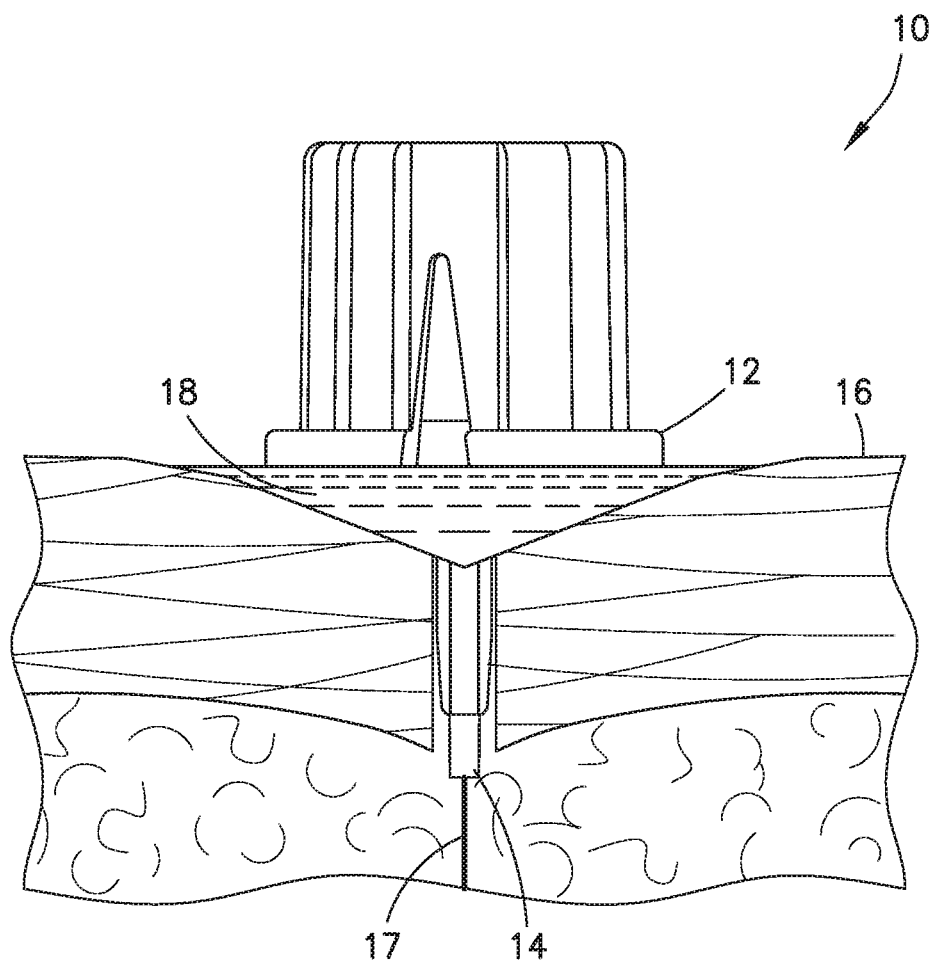
FIG. 1 illustrates a delivery device, such as an infusion set, with the catheter inserted into the patient.

Referring to FIG. 1, the delivery device is shown as an infusion set 10 having a base 12 and a cannula and/or catheter 14 extending from the base 12 for insertion into the skin 16 of the patient. The cannula 14 can be a hollow steel needle or a thin flexible catheter as known in the art. As used herein the term cannula is intended to refer to a rigid needle, rigid cannula or a flexible catheter. The cannula 14 or catheter is positioned in the patient by an insertion needle 17 as shown in FIG. 1 and as known in the art. The insertion device is actuated to penetrate the skin and position the cannula at the desired depth. The insertion needle is then retracted and the infusion set 10 connected to a suitable pump or delivery device for introducing the substance, such as insulin, through the cannula to the patient.

FIG. 1 illustrates the introduction or infusion of the fluid, such as the insulin, into the infusion site. In some incidences, the fluid can leak around the cannula 14 at or around the infusion site of the cannula 14 by improper placement of the cannula or by the cannula moving during use. The leaking fluid can form a pool 18 as shown in FIG. 1. The pool 18 is generally located below the infusion set or delivery device where the leakage is not readily visible by the patient.

The delivery device as illustrated in FIG. 2 is a patch pump assembly 20. The patch pump assembly 20 is a self-contained assembly as known in the art. The patch pump generally includes a reservoir containing the fluid such as insulin, which is typically insulin, and a pump assembly connected to suitable electronic controls to operate the pump assembly and deliver the fluid at the desired controlled rate. A battery or other power source is included to operate the device. The patch pump is attached to the skin of the patient with a cannula or catheter inserted into the patient for continuous and controlled delivery for a predetermined period of time.

Figure 5:
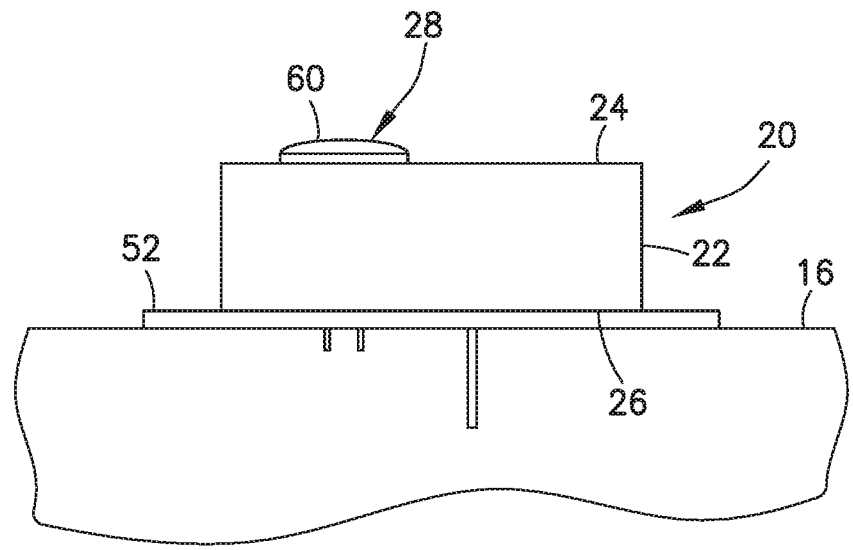
FIG. 5 is side view of the delivery device with the cannula inserted into the patient and the electrodes of the leak detector unit oriented to contact the skin and fluid leaking from the infusion site.
Figure 6:
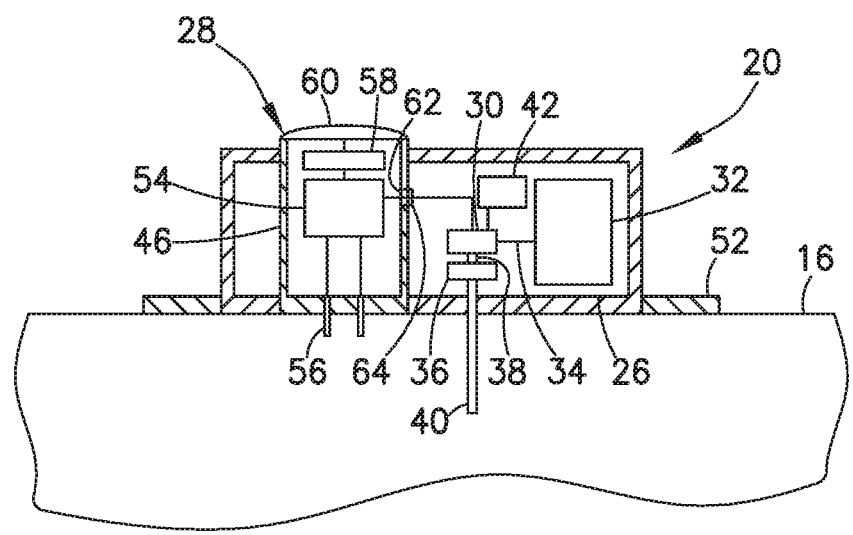
FIG. 6 is cross sectional side view of the delivery device of FIG. 5.

As shown in FIG. 2, the patch pump 20 is exemplary of the delivery device and has a housing 22 with a top wall 24 and a bottom wall 24. A cannula 40 extends from the bottom wall as shown in FIGS. 5 and 6 for positioning in the patient. A leak detector unit 28 is connected to the delivery device during use to detect leakage at the infusion site around the cannula 40. The leak detector unit 28 in the embodiment shown is a separate unit from the patch pump 20 and can be removed for re-use by connecting to a new delivery device, patch pump or infusion set. The delivery device can be used with the lead detector unit 28.

In the embodiment shown in FIG. 6, the housing 22 has an opening 44 for receiving the leak detector unit 28 and operatively connecting the leak detector unit to a pump assembly 30 contained within the housing 22. The pump assembly 30 is connected to a fluid reservoir 32 by a conduit 34. In embodiments of the device, the fluid within the reservoir 32 is insulin. The pump assembly is connected to a control valve 36 by a conduit 38 for delivering the insulin to the cannula 40 or catheter for introducing the insulin to the patient. A control unit 42 having a power source, such as a battery, is connected to the pump assembly 30 and valve 36 to control and stop the delivery of the insulin when needed.

In the embodiment shown in FIG. 2, the housing has the opening 44 in the top wall 24 for receiving the leak detector unit 28. In other embodiments, the opening can be formed in the side wall or bottom wall in a location that is able to support the leak detector unit 28 without interference with the operation of the patch pump 20. The insulin leak detector unit 28 in the embodiment shown preferably has the form of a small cylinder although other shapes and configurations can be used. The leak detector unit 28 has a housing 46 conforming to the shape and dimension of the opening 44.

As shown in FIG. 2, the opening 44 has a slot 48 or notch in the side edge having a shape complementing a key 50 on the outer surface of the wall of the housing 46 of the leak detector unit 28 to correctly position the leak detector unit 28 in the opening 44. FIG. 3 shows the leak detector unit 28 aligned with the opening 44 during insertion into the housing 22. FIG. 4 shows the leak detector unit 28 inserted into the housing in the operative position. In the embodiment shown in FIGS. 3 and 4 the patch pump 20 has a flexible base 52 on a bottom surface for attaching to the patient by an adhesive.

As shown in FIG. 6 the leak detector unit 28 includes an electrochemical sensor that includes an electrical circuit 54 and electrical components for detecting the leakage of the insulin or other fluid at the cannula infusion site and for actuating and controlling the valve 36 and/or pump assembly 30. Electrodes 56 extend from the bottom of the housing 46 of the leak detector unit 28. The electrodes are connected to the circuit 54 and are capable of detecting the fluid or stabilizers contained in the infusion formulation. As shown in FIGS. 5 and 6, the electrodes 56 project from the bottom end of the leak detector unit 28 for contacting the skin of the patient and the insulin or other fluid leaking from around the cannula during use. The leak detector unit 28 is preferably oriented in the patch pump 20 at a location at or near the cannula 40 so that the electrodes contact the insulin leaking from the infusion site. Preferably the electrodes are positioned relative to the cannula 40 so that minimal leakage occurs before the electrodes contact the insulin or other fluid so that the control circuit 54 is able to control and/or stop the flow of the fluid to the cannula.

A power source such as battery 58 is contained within the housing 46 and connected to the circuit 54 for operating the unit. The battery 58 powers a small potentiostat of the circuit 54 which sends voltage to the electrodes and measures a current produced when insulin contacts the electrodes. The current measured when the electrodes 56 contact the insulin and the circuit 54 produce a signal as an indicator of the leakage of the insulin at the infusion site. The circuit 54 is electrically connected to the micro-valve 36 and/or pump assembly 30 positioned upstream from the insulin infusion cannula for controlling the flow of the insulin. In one embodiment, the signal produced by the potentiostat in the circuit 54 actuates the valve 36 to close the valve 36 when leakage is detected to control and/or stop the flow of insulin and reduce or prevent further leakage at the infusion site. In other embodiments, the signal is produced by the circuit 54 stops the pump assembly 30 to stop the flow of insulin and prevent or reduce further leakage at the infusion site. In further embodiments, the control circuit 54 controls the flow rate by the pump to reduce or adjust the flow to reduce or minimize leakage at the infusion site. Corrective measures can then be taken by the patient to properly insert or position the patch pump and/or cannula so that the supply of insulin and infusion can be restarted.

Figure 8:
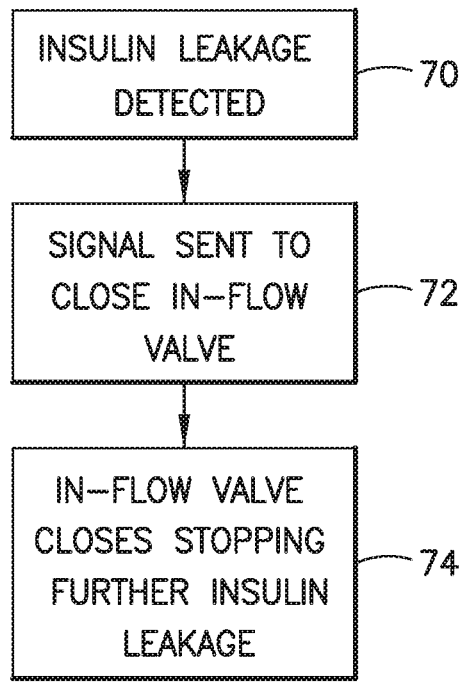
FIG. 8 is a flow chart of the operation of the leak detector unit.

FIG. 8 illustrates a method according to an exemplary embodiment of the invention. First, insulin leakage is detected by the circuit 54 of the electrochemical sensor indicated by block 70. Next, upon detection, a signal is sent indicated by block 72 to close the in-flow valve. Last, the in-flow valve closes upon detection indicated by block 74, stopping further insulin leakage.

In the embodiment shown in FIG. 6 an indicator, such as an indicator light 60, is positioned at the top end of the leak detector unit 28 that is visible to the patient. The indicator light 60 is connected to the circuit 54 and battery 58 and can be activated when the leakage is detected to signal the patient that corrective measures are needed. The use-life of the leak detector unit 28 is preferably at least 30 days to as long as 90 days.

As shown in FIGS. 2-4 the leak detector unit 28 is a separate, standalone self-contained unit that is removable from the delivery device and patch pump 20 for replacement or for inserting in a new delivery device or patch pump. In one embodiment, the delivery device is operable without the leak detector unit 28 coupled to the delivery device. The housing of the leak detector unit 28 includes an electrical contact 62 connected to the circuit 54. The electrical contact 62 is positioned on the outer surface of the housing to mate with a complementing electrical contact 64 in the opening in the housing 22 for forming the electrical connection between the leak detector unit 28 and the pump assembly 30 and/or control valve 36.

The patch pump 20 as known in the art has the reservoir 32 with a known amount of insulin or other fluid for delivering to the patient. At the end of the prescribed time of use, the patient must replace the patch pump. The leak detector unit 28 is removed from the patch pump 20 and inserted in a new patch pump 20 or infusion set.

The leak detector unit 28 is able to detect the presence of insulin or other fluid at the infusion site. The electrodes 56 can be formed on a bottom face of the unit 28 to contact the skin of the patient. The electrodes can be wires, a conductive film or other form that is able provide electrical contact with the insulin. The electrodes can be configured to measure a change in capacitance to detect the presence of the insulin. In one embodiment, the bottom face of the leak detector unit 28 has a hydrogel contacting or covering the electrodes so that when the insulin is absorbed by the hydrogel, the hydrogel conducts electricity between the electrodes which can be measured as an indication of leakage. The potentiostat applies a voltage across the electrodes and measures the current as an indication of the leakage of the insulin and an electrical connection with the circuit 54. Other methods can be used for electrically detecting the presence of the insulin or compounds contained in the insulin such as m-cresol or phenol.

In the embodiments described, the cylindrically shaped insulin leakage detector which is removed once the use life of either an infusion set or a patch pump has been reached. In other embodiments, the insulin leakage detector unit can be an integral part of the delivery device such as an infusion set or an insulin patch pump.

Exemplary embodiments of the present invention include a leakage detector controlled valve to stop insulin flow. A re-useable insulin leakage detector is preferably used when either a new infusion set or a new infusion pump is deployed.

Figure 7:
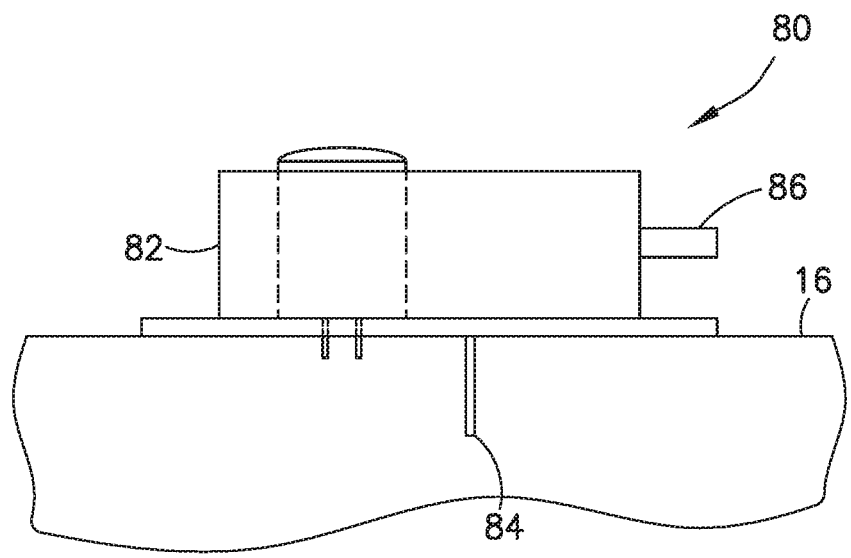
FIG. 7 is a side view of another embodiment of the delivery device.

In the embodiment of FIGS. 2-6, the delivery device is a patch pump although the leak detector unit 28 can be connected to and used with an infusion set or other delivery device. In the embodiment of FIG. 7, the delivery device 80 is similar to the previous embodiment by including a housing 82 with a cannula 84 for delivering the insulin or other substance. A supply tube or conduit 86 is connected to the device 80 to supply the insulin to the cannula from a storage reservoir. The pump assembly and control circuit can be formed as a separate unit from the infusion set. As in the previous embodiment, the leak detector unit 28 connects to the device 80 for connecting to a control for a valve within the device 80 and closing the valve when an insulin leak is detected.

The electrochemical sensor can detect the m-cresol or phenol insulin stabilizer, although other detection methods may be used without departing from the scope and spirit of the invention. One advantage of embodiments of the invention is fast stoppage of insulin flow upon leakage detection without the requirement of visual identification by the patient.

The above description of the embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A fluid delivery assembly for introducing a fluid to a patient, said delivery assembly comprising;
- a delivery device adapted for delivering a fluid to the patient, the delivery device having a housing and a base with a bottom face for attaching to the skin of the patient, and a cannula extending from said bottom face for penetrating the skin of the patient at a delivery site;
- a pump assembly connected to a fluid reservoir and said cannula for delivering the fluid through the cannula to the patient; and
- a removable leak detector unit coupled to said housing of said delivery device and oriented for detecting leakage of the fluid at the delivery site, said leak detector operatively connected to said pump assembly when coupled to said housing to stop said pump assembly when leakage is detected at the delivery site to stop the flow of the fluid.

2. The fluid delivery assembly of claim 1, wherein said leak detector is a self-contained unit that is separable from the delivery device and said pump assembly, and where said pump assembly and fluid reservoir are enclosed in said housing.

3. The fluid delivery assembly of claim 2, wherein said leak detector includes electrodes extending from said leak detector unit and from said bottom face of said delivery device for contacting fluid leaking at the infusion site.

4. The fluid delivery assembly of claim 1, wherein said delivery device is a patch pump including said housing enclosing said pump assembly, a fluid reservoir, and said cannula, said housing having an opening for removably receiving said leak detector unit, said leak detector unit having an electrical contact connecting with said pump assembly for actuating said pump assembly to stop the flow of the fluid when leakage is detected.

5. The fluid delivery assembly of claim 4, wherein said leak detector unit is a self-contained unit enclosing a power source, an electrical sensing circuit for sensing leakage at the infusion site and controlling said pump assembly.

6. The fluid delivery assembly of claim 5, wherein said electrical sensing circuit includes electrodes oriented for contacting and detecting leakage at the infusion site.

7. The fluid delivery assembly of claim 6, wherein said pump assembly includes a valve for controlling the flow of the fluid, and where said leak detector unit is operatively connected to said valve to close said valve when leakage is detected.

8. The fluid delivery assembly of claim 7, wherein said electrical sensing circuit detects the presence of at least one compound in the fluid.

9. The fluid delivery assembly of claim 8, wherein said fluid is insulin and said at least one compound is m-cresol or phenol.

10. The delivery device of claim 1, wherein said housing has an opening configured to receive said removable leak detector, where at least a portion of said leak detector projects from said bottom face of said base and is operatively connected to said pump assembly when received in said opening in said housing.

11. An insulin leakage detector and insulin delivery device, comprising,
- an electrochemical sensor having electrodes located at a patient facing surface of the infusion device, the sensor detecting the presence of insulin;
- a valve between an insulin reservoir and a delivery cannula of said delivery device capable of stopping insulin flow, wherein the sensor sends a signal to the valve upon detection of the presence of insulin, and the valve stops the flow of insulin upon receipt of the signal.

12. The insulin leakage detector of claim 11, wherein the insulin delivery device is an infusion set.

13. The insulin leakage detector of claim 11, wherein the insulin delivery device is a patch pump.

14. A delivery device comprising;
- a housing having a base and a cannula for introducing insulin to a patient at a delivery site;
- a pump assembly in said housing for supplying the insulin to the cannula; and
- a leak detector unit for detecting leakage of the insulin at the delivery site, said leak detector being operatively connected to said pump assembly to stop the flow of insulin when said leak detector unit is coupled to said housing and operatively connected to said pump assembly and when leakage is detected at the delivery site, and where said leak detector unit is removably coupled to said housing.

15. The delivery device of claim 14, wherein said leak detector unit is a self-contained unit having a housing, at least one electrode configured for contacting the insulin leaking from the delivery site, said leak detector unit housing enclosing an electrical circuit sensing device connected to said at least one electrode for sensing insulin contacting the at least one electrode and producing a signal to stop the flow of insulin to said cannula, and a power source for operating said electrical circuit.

16. The delivery device of claim 15, wherein said electrical circuit is operatively connected to said pump assembly, and where said signal actuates said pump assembly to stop a flow of insulin to said cannula.

17. The delivery device of claim 16, wherein said housing has an opening with a dimension to receive said leak detector unit, said housing having a bottom end with an opening to enable said at least one electrode to extend from the bottom end of the housing to contact insulin leaking from said delivery site.

18. The delivery device of claim 17, wherein said opening in said housing has a notch in a peripheral edge and said leak detector unit has a key complementing said notch to orient said leak detector unit in a selected position relative to said housing.

19. The delivery device of claim 17, wherein said housing of said leak detector unit has an outer surface with an electrical contact connected to said electrical circuit, and said housing of said delivery device has an electrical contact connected to said pump assembly, said electrical contact of said housing of said delivery device being positioned to mate with said electrical contact of said leak detector unit when said leak detector unit is received in said opening in said housing.

20. The delivery device of claim 16, wherein said pump assembly comprises a valve and where said leak detector unit is operatively connected to said valve to stop the flow of insulin when leakage is detected at the delivery site.

* * * * *